United States Patent [19]

Abe et al.

[11] Patent Number: 4,513,751

[45] Date of Patent: Apr. 30, 1985

[54] METHOD FOR MEASURING OXYGEN METABOLISM IN INTERNAL ORGAN OR TISSUE

[75] Inventors: Hiroshi Abe, No. 7-2, Fundo-cho, Nishinomiya-shi, Hyogo; Nobuhiro Sato, No. 1-5-11, Tachibana-cho, Toyonaka-shi, Osaka; Kimizo Ono; Kazuo Hirano, both of Osaka, all of Japan

[73] Assignees: Sumitomo Electric Industries, Ltd.; Hiroshi Abe; Nobuhiro Sato, all of Osada, Japan

[21] Appl. No.: 474,273

[22] Filed: Mar. 11, 1983

Related U.S. Application Data

[63] Continuation of Ser. No. 128,064, Mar. 7, 1980, abandoned.

[30] Foreign Application Priority Data

Mar. 7, 1979 [JP] Japan .................................. 54-27183

[51] Int. Cl.[3] ............................................. A61B 5/02
[52] U.S. Cl. ...................................... 128/666; 128/633
[58] Field of Search .......................... 128/4–8, 128/303.1, 395, 397, 634, 637, 665, 666; 604/20

[56] References Cited

U.S. PATENT DOCUMENTS

| | | | |
|---|---|---|---|
| 3,068,742 | 12/1962 | Hicks | 128/634 |
| 3,690,769 | 9/1972 | Mori | 128/6 |
| 3,814,081 | 6/1974 | Mori | 128/634 |
| 3,822,695 | 7/1974 | Takayama | 128/634 |
| 3,825,342 | 7/1974 | Lubbers et al. | 128/634 |
| 4,114,604 | 9/1978 | Shaw et al. | 128/634 |
| 4,170,987 | 10/1979 | Anselmo et al. | 128/665 |
| 4,201,222 | 5/1980 | Haase | 128/634 |
| 4,222,389 | 9/1980 | Rubens | 128/666 |
| 4,261,344 | 4/1981 | Moore et al. | 128/6 |

*Primary Examiner*—Edward M. Coven
*Assistant Examiner*—Max F. Hindenburg
*Attorney, Agent, or Firm*—Sughrue, Mion, Zinn, Macpeak & Seas

[57] ABSTRACT

A method for measuring the metabolic utilization rate of oxygen in an internal organ or tissue, wherein a portion of the organ or tissue to be diagnosed is subjected to interruption of oxygen supply and then measured biospectroscopically. Reflection spectral characteristic variations per unit of time are measured. The measured information is converted into an electrical signal to indicate the metabolic rate.

7 Claims, 5 Drawing Figures

METHOD FOR MEASURING OXYGEN METABOLISM IN INTERNAL ORGAN OR TISSUE

This application is a continuation of application Ser. No. 128,064 filed Mar. 7, 1980, now abandoned.

BACKGROUND OF THE INVENTION

The present invention relates to a method for measuring the metabolic rate of oxygen, that is, the rate at which oxygen is utilized, in an internal body organ or tissue. More particularly, the invention relates to such a method in which variations per unit of time of the reflection spectrum of the organ or tissue are measured using biospectrometry.

Conventionally, in clinical diagnosis and medical research, visual observation of internal organs or tissue is an important diagnostic technique. Using recently available methods, various parts of internal organs can be directly observed macroscopically utilizing an optical transmission system, for example, optical fibers such as those employed in a gastro camera, to thus greatly improve clinical diagnosis. However, such macroscopic observation cannot provide objective and quantitative diagnosis since it depends largely on the doctor's skill and experience. Further, the oxygen metabolism of the organ tissue is commonly determined by excision of a portion of the tissue or calculated by comparing the venous and arterial pressures of the blood flow from and to the organ and the flow rate thereof. These techniques are, unfortunately, often accompanied by infection of the organ or tissue being examined.

SUMMARY OF THE INVENTION

It is therefore an object of the present invention to overcome the above-mentioned drawbacks and to provide a novel method for accurately measuring the metabolic rate of a designated organ or tissue.

Another object of this invention is to provide such a method capable of measuring the metabolic rate without danger of infection.

Still another object of this invention is to provide such a method capable of uncovering abnormalities in the metabolic rate of an internal organ in the early stages of the underlying problem which gives rise to the abnormality.

Still another object of this invention is to provide such method for uncovering such metabolic abnormalities before their cause could be determined using macroscopic techniques.

Briefly, and in accordance with the present invention, the internal organ or tissue to be diagnosed is first subjected to interruption of oxygen supply (for example, by pressurization), and then the reflection spectral characteristic variations per unit of time of the organ or tissue are measured. The amount of variation is indicative of the metabolic rate of the internal organ or tissue. The pressurization value may be higher than the maximum normal blood pressure.

DESCRIPTION OF THE PREFERRED EMBODIMENTS

Figure 1:
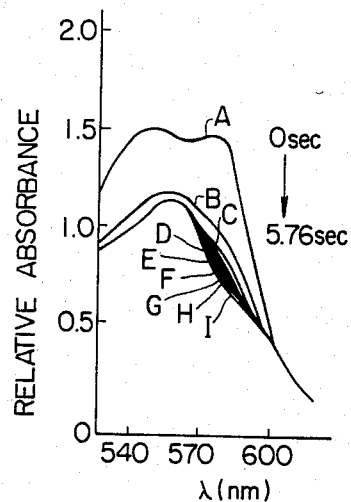
FIG. 1 is a graphical representation showing diffused reflection spectral variations per unit of time of an internal organ after interruption of its oxygen supply.

The present invention is based on a discovery with respect to the reflection spectrum characteristic variations per unit of time using biospectroscopic measurements, and the technical improvement of the invention is ascribed to the discovery. FIG. 1 shows a reflection characteristic of the part of the internal organ or tissue, the oxygen supply to which is interrupted. The horizontal and vertical axes indicate wavelength and relative light absorbance, respectively.

An uppermost curve A is obtained during oxygen supply to the internal organ, whereas the remaining curves B through I are obtained during interruption of oxygen supply to the designated part of the organ. These curves show spectral variations per unit of time. As is apparent from the curve A, observed are two peaks of oxyhemoglobin (hereinafter referred to simply as "oxy-Hb") in the blood flow in the organ. On the other hand, after interruption of the oxygen supply (after pressurization), the relative absorbance is greatly reduced, and the spectral pattern is greatly changed, as shown by curves B to I.

Figure 2:
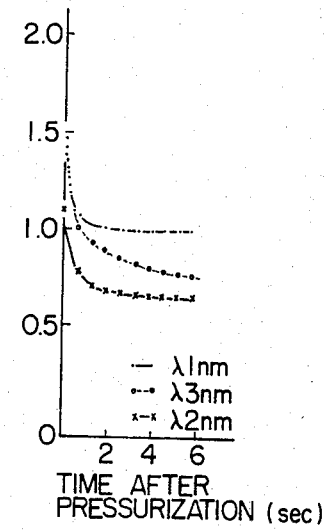
FIG. 2 is a graphical representation showing the relationship between time after pressurization and relative absorbance of deoxyhemoglobin and oxyhemoglobin.

Further, as shown in FIG. 2, the decrease of the absorbance is terminated at isobestic wavelengths, corresponding to a balance between oxy-Hb and deoxyhemoglobin (hereinafter referred to simply as "deoxy-Hb"), about 1 to 2 seconds after the pressurization for wavelengths of $\lambda_1$ and $\lambda_2$, for example, 569 nm and 586 nm, respectively. On the other hand, the decrease of the absorbance at the peak point at a wavelength $\lambda_3$ (for example, 577 nm) for oxy-Hb continues beyond the point where the $\lambda_1$ and $\lambda_2$ curves level out after a few seconds.

The absorbance decrease for about 1 to 2 seconds is considered to be due to a decrease in the amount of Hb. The decrease of the amount of Hb is attributed to the expulsion of almost all of the blood in the local blood path due to pressurization since the absorbances at the wavelengths $\lambda_1$ and $\lambda_2$ are simultaneously reduced.

On the other hand, the continuing absorbance reduction at the wavelength of $\lambda_3$ is considered to be due to conversion of oxy-Hb into deoxy-Hb due to an absorbance increase adjacent to a point of inflection of the absorbance curve wavelength at $\lambda_4$ (for example, 555 nm) for oxy-Hb. That is, local blood flow is completely blocked due to pressurization, and residual oxygen is consumed due to metabolism of local cells, so that all of the Hb is converted to deoxy-Hb.

Therefore, measurement of the variations per unit of time of the characteristic curves corresponding to the conversion of oxy-Hb to deoxy-Hb, i.e., the measurement of the metabolic function, can be made by measuring the reflection spectrum for the constant or equi-absorbance points ($\lambda_1$, $\lambda_2$ curves)(relating to oxy-Hb and deoxy-Hb), and the characteristic curve at wavelength $\lambda_3$ for either one of oxy-Hb and deoxy-Hb.

According to the foregoing description, the peak point $\lambda_3$ for oxy-Hb is regarded as a characteristic wavelength. However, it is also possible to conduct measurements using an inflection point for oxy-Hb or a peak or inflection point for deoxy-Hb.

Figure 3:
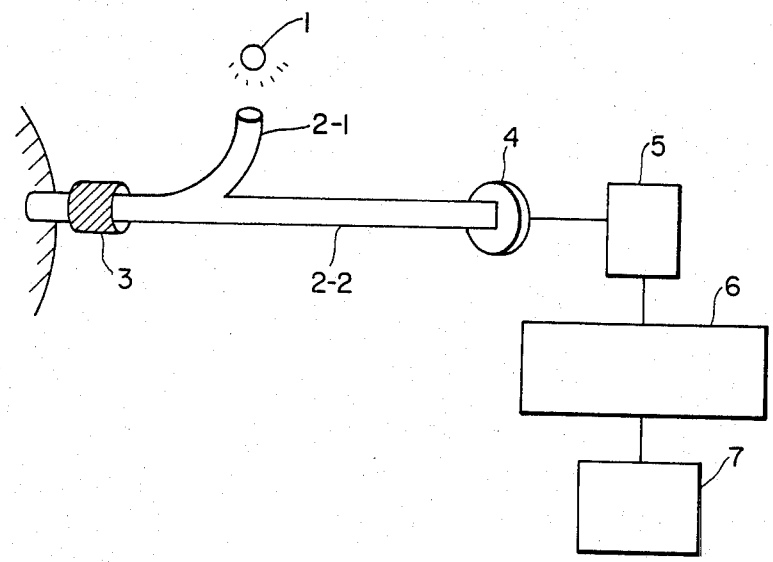
FIG. 3 is a schematic view showing an apparatus for conducting a method of this invention.

One preferred embodiment of an apparatus for measuring the metabolic function according to the present invention is shown in FIG. 3, wherein light source 1 such as a tungsten-iodine lamp, a xenon lamp, or a mercury lamp emits a broad spectrum of light. Reference numeral 2-1 designates an optical fiber used to introduce light from the light source 1 to an internal organ to be examined. Reference numeral 2-2 designates a second optical fiber adapted to introduce light reflected from the organ to a light splitting device such as a spectroscope 4. Further, a pressurization control portion 3 is provided for interrupting oxygen supply the organ. Such a device is known in the art, for example for U.S. Pat. No. 4,213,462. The pressurization force should be higher than the maximum blood pressure. The light source 1 and the optical fiber 2-1 may not be required in a particular measuring environment, depending also on the reflection factor of the portion to be measured.

At the light splitting device 4, light at a specific wavelength is selected and is introduced to a photoelectric transducer 5 where the light is converted into an electrical signal. The electrical signal is processed by a processing unit 6, and the measured metabolic function is displayed by an indicator 7.

Figure 4:
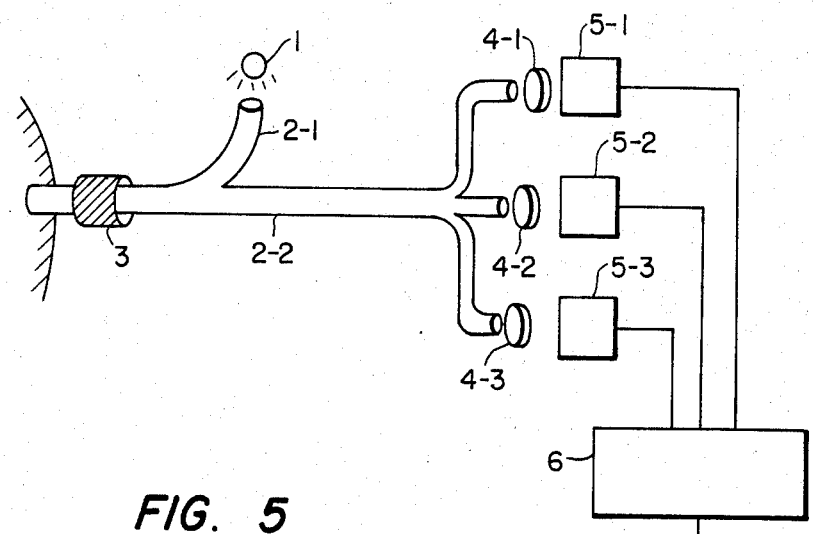
FIG. 4 is a schematic view showing an apparatus for conducting a method of this invention, wherein light splitting means and related components are illustrated in more detail.

According to an embodiment shown in FIG. 4, a plurality of optical fibers are formed as a fiber bundle 2-2. These fibers are divided into groups, for example, three groups corresponding to three different wavelengths to be measured. Further, corresponding filters 4-1, 4-2 and 4-3 having different transmission wavelengths $\lambda_1$, $\lambda_2$ and $\lambda_3$ are provided to receive and separate the respective light signals. The separated light signals are converted into electrical signals by respective photoelectric transducers 5-1, 5-2, and 5-3.

Figure 5:
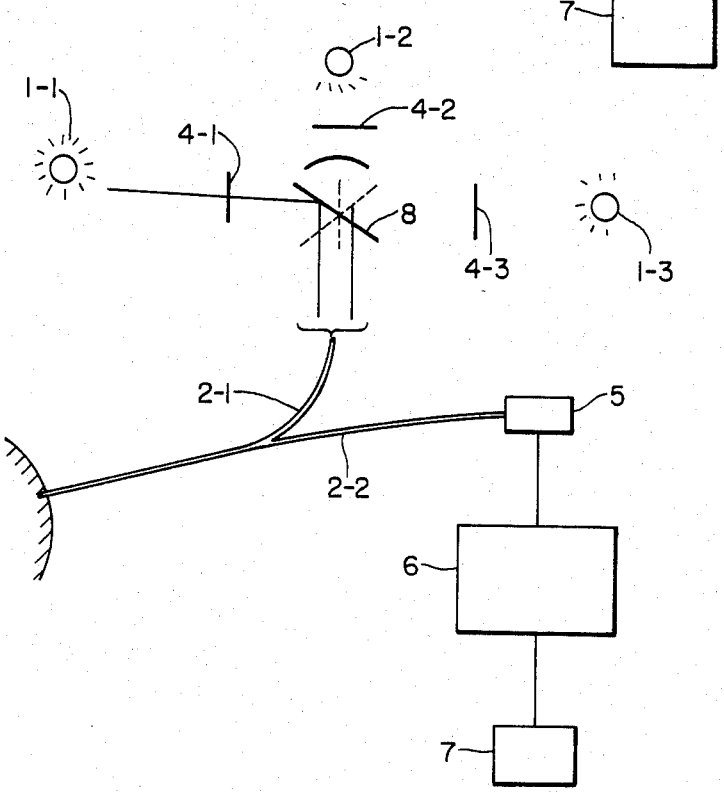
FIG. 5 is a schematic view showing another embodiment of the apparatus for conducting a method of this invention.

Another embodiment according to the present invention is shown in FIG. 5, wherein like parts and components are designated by the same reference numerals as those shown in the foregoing embodiments. In the embodiment shown in FIG. 5, the separated light signals are directed toward a portion to be measured. Light sources 1-1, 1-2, and 1-3 are positioned at different locations. Filters 4-1, 4-2 and 4-3 are provided for separating the received light signals at wavelengths from corresponding light sources. Further, a rotary mirror 8 is provided for selectively orienting one of the light beams toward an optical fiber 2-1 provided to introduce the light signals to the portion to be measured. The rotation of the rotary mirror 8 is controlled by a processing circuit 6. An optical fiber 2-2 is provided to transmit the light reflected from the position to be measured to a photoelectric transducer 5. Reference numeral 7 designates an indicator for indicating the measured metabolic function. According to this embodiment, the pressurization member is omitted. If the operator can maintain constant pressurization, such member is not strictly required.

The optical fibers 2-1 and 2-2 can be replaced by other types of light transmitting devices. Further, the light splitting device can be implemented with an interference filter, an interference mirror, an optical prism or a spectroscope. Furthermore, the photoelectric transducer may be an image sensor array, a photo transistor, a photo-multiplier or solar battery.

According to the embodiment shown in FIG. 3, the measurement can be made regardless of external ambient light, and therefore it is unnecessary to conduct the measurement in a dark room.

In view of the foregoing discussion, according to the present invention, the metabolic rate for oxygen of an internal organ or tissue can be measured without danger of infection by the use of interruption of the oxygen supply to the organ, so that quantitative diagnosis as to the local metabolic rate becomes possible. Further, abnormalities of metabolic rate which cannot be detected using microscopic techniques can be uncovered. Technically, since the spectral reflectance variations per unit of time are the measured quantity, no severe requirements as to the spectral characteristics are imposed, to thus provide a compact and simple apparatus.

While the invention has been described in detail and with reference to specific embodiments thereof, it will be apparent to one skilled in the art that various changes and modification can be made thereto without departing from the spirit and scope of the invention.

What is claimed is:

1. A method for measuring the metabolic rate for oxygen in an internal organ or in a tissue, comprising the steps of:
   (a) interrupting the oxygen supply to a portion of said organ or tissue to be diagnosed by applying pressure at a predetermined point;
   (b) directing light onto said portion;
   (c) sensing a first spectral characteristic of light reflected from said portion at at least one first wavelength, said first spectral characteristic varying in absorbance rapidly to a constant value following said step of interrupting said oxygen supply, and sensing a second spectral characteristic at at least one second wavelength of said reflected light, said second spectral characteristic continuing to change in absorbance after said first characteristic at said first wavelength has reached said absorbance constant value; and
   (d) determining a rate of change of said second characteristic relative to said first characteristic after said first characteristic has reached said constant absorbance level said rate of change being indicative of the metabolic rate.

2. A method as defined in claim 1, wherein a portion of said organ and tissue is subject to pressurization at a pressure higher than the maximum blood pressure.

3. A method as defined in claim 1, wherein an optical fiber means is used as a light transmission means in the measurement of said reflection spectrum characteristic variation per unit time, which measurement is performed by light processing means.

4. A method as defined in claim 1, wherein a bundle of fibers are used for a light receiving optical system, said bundle of fibers being divided into a plurality of fibers for transmitting respective light signals each having a required wavelength, said light signals each being passed through a corresponding filter having a predetermined transmission wavelength.

5. A method as defined in claim 1, wherein said light from said portion to be diagnosed is initially transmitted thereinto by a light source, the light emitted from said light source being subject to filtering.

6. A method as defined in claim 3, wherein said optical fiber means comprises a light receiving optical system further comprised of a bundle of fibers, said bundle of fibers being divided into a plurality of fibers for transmitting respective lights each having required wavelength, said lights being passed through corresponding filters each having predetermined transmission wavelengths.

7. A method as defined in claim 3, wherein said light from said portion to be diagnosed is initially transmitted thereinto by a light source, the light emitted from said light source being subject to filtering.

* * * * *